United States Patent
Scheuch et al.

(12) United States Patent (10) Patent No.: US 6,571,791 B2
Scheuch et al. (45) Date of Patent: Jun. 3, 2003

(54) INHALATION DEVICE

(75) Inventors: Gerhard Scheuch, Gemünden (DE); Knut Sommerer, München (DE); Friedel Haas, Gauting (DE); Bernhard Müllinger, Unterdietfurt (DE); Sascha Roeder, Ingolstadt (DE)

(73) Assignee: InAMed GmbH, Gemünden (DE)

( * ) Notice: Subject to any disclaimer, the term of this patent is extended or adjusted under 35 U.S.C. 154(b) by 46 days.

(21) Appl. No.: 09/879,477

(22) Filed: Jun. 12, 2001

(65) Prior Publication Data

US 2002/0017293 A1 Feb. 14, 2002

(30) Foreign Application Priority Data

Jun. 14, 2000 (DE) .......................................... 100 29 119

(51) Int. Cl.[7] .............................................. A61M 11/00
(52) U.S. Cl. .................................................. 128/200.22
(58) Field of Search ........................ 128/200.22, 200.23, 128/203.12, 205.14, 205.15

(56) References Cited

U.S. PATENT DOCUMENTS 5,613,489 A * 3/1997 Miller et al. ........... 128/203.28

FOREIGN PATENT DOCUMENTS

| DE | 199 12 461 A1 | 9/2000 |
|----|---------------|--------|
| EP | 0 050 654 B1 | 12/1985 |
| EP | 0 352 412 A2 | 4/1989 |
| EP | 0 965 355 A2 | 12/1999 |

OTHER PUBLICATIONS

Bauernfeind, JC. "The Safe Use Of Vitamin A". The Nutrition Foundation, Washington, DC, 1980.

* cited by examiner

Primary Examiner—William C. Doerrler
Assistant Examiner—Malik N. Drake
(74) Attorney, Agent, or Firm—Eugene Stephens & Associates

(57) ABSTRACT

An inhalation device has a container 2 for an aerosol volume inhaled via a channel 15 and a mouthpiece 14, the container being located within a housing 12. The aerosol, in particular vitamin A, is introduced from a cartridge 17 into the interior of the container 2 via a nebulizer 18. The breath flow in the inhalation device is controlled via a control means 5 that keeps the inhalation flow essentially constant during the entire inhalation period.

27 Claims, 7 Drawing Sheets

INHALATION DEVICE

FIELD OF THE INVENTION

Figure 1:
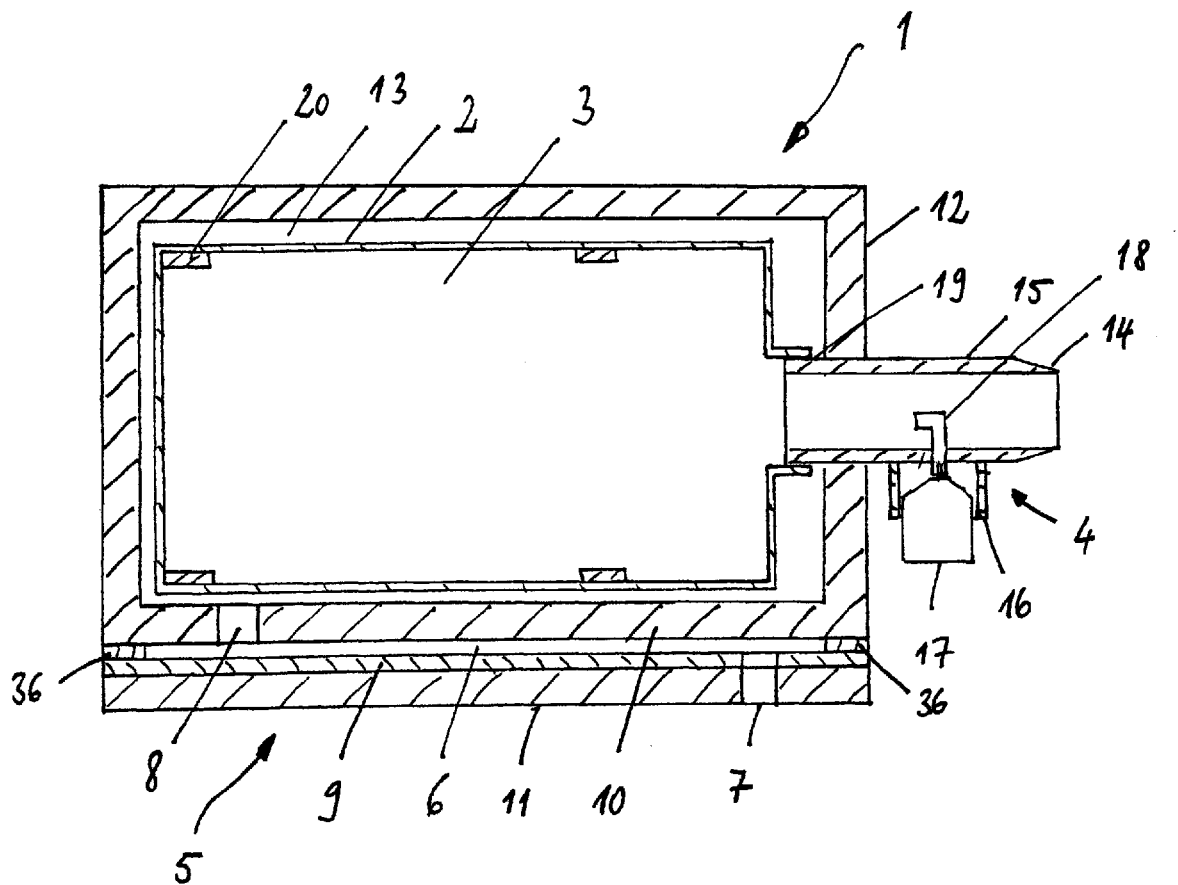

The invention relates to a device for inhaling dosed pharmaceuticals in the form of an aerosol into the lungs. Suitable pharmaceuticals include analgesics, anti-angina agents, anti-allergics, antihistamines and anti-inflammatory agents, expectorants, antitussives, bronchodilators, diuretics, anticholinergics, corticoids, xanthins, anticancer drugs and therapeutically active proteins or peptides, such as insulin or interferon.

The administration of pharmaceuticals including vitamin A is particularly useful for treating respiratory diseases, such as asthma, and for the prophylactic treatment and therapy of the mucosae of the tracheobronchial tract.

BACKGROUND OF THE INVENTION

The term "vitamin A" stands for a number of chemically similar compounds producing different effects in human and animal organisms. Vitamin A is essential for man as a vitamin deficiency appears if the vitamin is not supplied together with food. A vitamin A deficiency shows up in various modifications in the skin, mucosae and eyes. Symptoms include a cornification (keratinisation) of the mucosae of the respiratory system or the connective tissue membrane of the eye and a higher disposition for infections and blindness, where the deficiency is pronounced. The majority of the modifications resulting from the deficiency, especially in the mucosae, can be repaired by a vitamin A supply. However, the systemic administration aiming at the repair, of for instance a pavement (squamous) epithelium metaplasia, or at the prevention of a recurrence of such modifications requires high concentrations, which can sometimes produce considerable side effects (cerebral pressure symptoms, disorders of the liver cell metabolism, etc.). Moreover, the use of preparations in high doses is contraindicated in pregnancy because of the risks of fetal deformation (Bauernfeind J. C.: The Safe Use of Vitamin A, The Nutrition Foundation, Washington D.C., 1980).

Moreover, in the case of a diet-caused protein deficiency and in the case of disorders of the liver cell metabolism, such as inflammation or cirrhosis, the supply of vitamin A even in physiological concentrations is banned, because the associated disorders of protein synthesis (deficient formation of the transport proteins) of the liver do not allow the vitamin to be eliminated from the storage organs into which it is transferred after resorption (absorption).

Furthermore, after systemic administration, the vitamin can only be taken up by the peripheral target tissues, such as the respiratory epithelium, and caused to exert its function, if it is bound to this very transport protein.

EP-A-0 352 412 describes the use of a preparation of esters of retinol and retinoic acid for administration by inhalation to solve this problem. This in particular allows the active ingredient to exert a topical action on the mucosae of the tracheobronchial tract of man and animal. This facilitates the prophylactic treatment and therapy of specific diseases and functional abnormalities, for instance of specific cellular differentiation disorders, pavement (squamous) epithelium metaplasia, neoplastic modifications, reduced activity of the ciliated epithelium and dysfunction of mucosa-forming cells. Moreover, this preparation can also be used for the therapy or as an adjuvant in the therapy of inter alia bronchial carcinoma, acute and chronic bronchites and the bronchopulmonary dysplasia of newborn children. Clinical studies reveal, however, that the application of vitamin A by inhalation using conventional inhalators only allows insufficient amounts of the active ingredient to be administered to the target tissue, the ciliated epithelium of the bronchial mucosa.

DE-A-199 12 461 by the same inventors as those named for the present patent application was published on Sep. 21, 2000 and is consequently a postpublished document. It discloses a device for limiting the flow at low differential pressures, in particular for limiting the inhalation flow volume during the inhalation of therapeutic aerosols. The device has a housing which comprises an inhalation opening, an exhalation opening, and a flow channel arranged therebetween and has a flat oblong cross section and flexible large-surface walls. Depending on the differential pressure between the inhalation opening and the exhalation opening and the flexibility of the wall material, the cross section of the flow channel can be reduced in size to suit a predetermined maximum inhalation flow volume.

Essentially, the administration of pharmaceuticals in the form of an aerosol to the lung by inhalation is influenced by four factors: (i) the particle size and particle properties of the aerosol; (ii) the volume inhaled by the patient in one breath; (iii) the patient's breath flow; and (iv) the patient's morphometry and respiratory system. Although aerosols in suitable particle size ranges are produced by the conventional systems, the parameters "one breath volume" and "breath flow" (rate of breathing) are taken into account either insufficiently or not at all. This leads to an uncontrolled inhalation of the aerosol, which in turn has the result that the aerosol particles reach the lung in insufficient amounts or do not reach the areas (for instance the alveolar area) within the lung to be treated.

EP-A 0 965 355 proposes a device for the controlled application of a measured amount of pharmaceuticals into the lung by inhalation. This controlled inhalator comprises a closed container which can be filled with a predetermined aerosol volume and from which the aerosol can be withdrawn via a control means for the inhalation flow. In this known inhalator, said control means is either an adjustable valve or a critical nozzle. The use of an adjustable valve or a critical nozzle allows the breath flow to be limited.

EP-B-0 050 654 proposes an inhalation device for the administration of pulmonary medication. This device has an inflatable envelope from which an aerosol can be inhaled through a mouthpiece. This aerosol is introduced via a nebulizer into the inflatable envelope from a cartridge prior to inhalation. In order to limit the amount of air flowing through the mouthpiece during inhalation, the mouthpiece has a restriction. This restriction limits the breath flow during inhalation.

The two above-mentioned inhalation devices are distinguished by the fact that the flow is limited, i.e. during the inspiratory phase, the breath flow rises only slowly and the breath flow increase decreases steadily, leading to a steady flattening of the curve in the graph of the breath flow versus time. The result of this flow limitation is that, depending on the patient's inspiratory capacity, the breath flow increases differently (and flattens) and, in the worst case, is insufficient for the treatment required. This means that the envisaged flow limitation of the known inhalators can lead to an insufficient aerosol deposition.

SUMMARY OF THE INVENTION

In light of this, the invention addresses the problem of providing an inhalation device, which, irrespective of the patient's characteristics, provides the breath flow required for the inhalation of aerosols, in particular vitamin A. This problem is solved by an inhalation device possessing the features of the claims.

The invention starts from the basic idea of providing a control means which keeps the inhalation flow at an essentially constant level during the entire inhalation period of the aerosol. This means that according to the invention, the inhalation flow increases right at the start of the inspiratory phase to its maximum value, which is required for adequate aerosol administration, and remains at this maximum value as long as the patient produces a minimum pressure during inhalation. This minimum pressure is preferably 10 mbar at the most and preferably lies in the range between 5 and 10 mbar. According to the invention, a flow limitation is thus provided even at low differential pressures.

The inhalation device according to the invention is a combination of a self-expanding container for a predetermined aerosol volume, a means for introducing aerosol from an aerosol dispenser into the container and a means for controlling the inhalation flow, the control means keeping the inhalation flow at an essentially constant level during the entire inhalation period.

According to the invention, the control means has a flow channel comprising an inlet opening and an outlet opening, which are spaced apart from each other and arranged at the two ends of the flow channel.

According to a first embodiment, the flow channel is formed by a flexible large-surface wall and an essentially stiff wall arranged in parallel thereto. The flexible wall is covered by a cover at the side facing away from the flow channel. The outlet opening of the flow channel preferably leads into the interior of a housing surrounding the aerosol container. Prior to being inhaled, the aerosol is introduced into the interior of the container, for instance from a cartridge, preferably via a nozzle, such as a nebulizer. In the course of this, the container expands until its interior, in the completely expanded state of the container, is filled with an aerosol volume predetermined by the volume of the container. As soon as a patient inspires the aerosol from the container via a mouthpiece, which is preferably provided, the container draws together because of the suction effect. The negative pressure forming in the interior of the container in consequence of this is compensated for by the flow channel. The negative pressure acting on it has the result that, depending on the degree of the negative pressure, the flexible wall bulges towards the interior of the flow channel and in this manner reduces its cross section. This reduction of the cross section results in a limitation of the air flow through the flow channel into the interior of the housing for pressure compensation, which in turn limits the aerosol flow from the container. Due to the control means of the invention, an automatic volume flow regulation of the flow channel, and thus an automatic breath flow regulation, is brought about at pressures as low as 5 mbar. The negative pressure formed during the inhalation of the aerosol results in a direct reduction of the cross section of the flow channel because of the flexible wall, i.e., in a direct reduction to a limit value. As a consequence of this, the breath flow limit value is achieved right at the start of inhalation and is maintained during the entire inhalation period at pressures of 80 to 100 mbar, as normally produced by the inspiration of the lung.

In a preferred embodiment, the essentially stiff wall of the flow channel has one or more oblong depressions or grooves which extend in the direction of the channel and are spaced apart from each other by corresponding ribs or ribs. The flexible wall, which preferably consists of a bio-compatible material such as silicone or rubber, bulges into the depressions during inhalation and rests on the ribs. The ribs prevent the flow channel from closing completely and limit the reduction of the channel's cross section.

According to an alternative embodiment, the flow channel is delimited by two flexible walls arranged in parallel and spaced apart from each other, which, depending on the negative pressure, bend towards the inside and thus reduce the cross section of the channel.

In a third embodiment, the control means is provided in the form of a cylindrical housing, with a circular flow channel being formed in the interior of this housing by two flexible cylindrical walls.

According to a fourth embodiment, the inhalation device of the invention possesses not only the self-expandable container and the introduction means for the aerosol but also a control means that comprises several flow channels which form a star and are situated between the ribs extending in the form of a star. These ribs support a circular flexible mat which, upon generation of a negative pressure in the flow channels, bulges into the flow channels as in the first embodiment and reduces the cross section, thus adjusting the flow volume to an essentially constant value. The ribs are either of the same length or at least one web is longer.

The means for introducing aerosol from an aerosol dispenser into the container prevents medication, such as vitamin A in the form of an aerosol, from being released directly from the aerosol dispenser into the mouth and inhaled. Rather, the patient is obligated to introduce the aerosol from the aerosol dispenser into the container and only then, with the use of the inhalation device of the invention, can the patient inhale the predetermined aerosol volume defined by the container. The aerosol dispenser, such as a cartridge, is preferably connected over a collar to a nozzle and is held at the inhalation device. The aerosol is then introduced into the interior of the container via the nozzle. Other preferred features are specified in the dependent claims.

The inhalation device preferred according to the invention has numerous advantages. The inhalation device permits uniform and precise dosing of the medication, irrespective of the patient's coordination ability. Different volumina of the container allow the desired deposition site in the lung and also the desired amount of aerosol to be preselected. If the housing is at least in part made transparent, the inhaled volume can be visually controlled, as the patient sees the container folding up. The inhalation device is easy to handle and at the same time highly effective. With the introduction of the active ingredient into the container prior to inhalation, the aerosol release from the dispenser is limited to the necessary amount, thus preventing excessive consumption. The precise and efficient dosing in turn leads to low costs of treatment, for instance with vitamin A. Another advantage of the invention is the fact that the use of a propellant is not absolutely necessary, for instance for the administration of vitamin A.

Figure 10A:
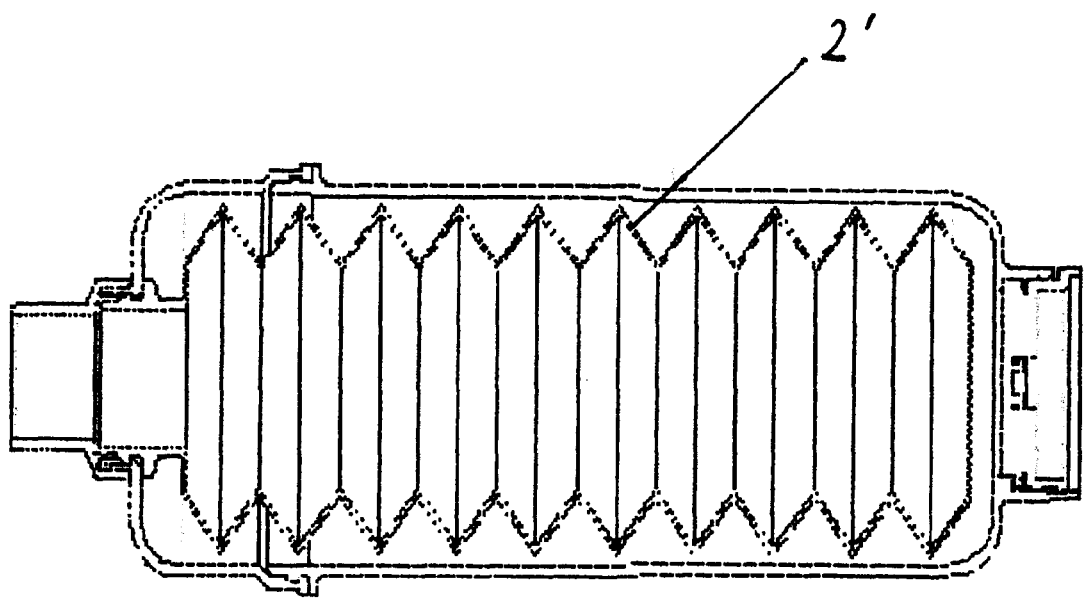
Figure 10B:
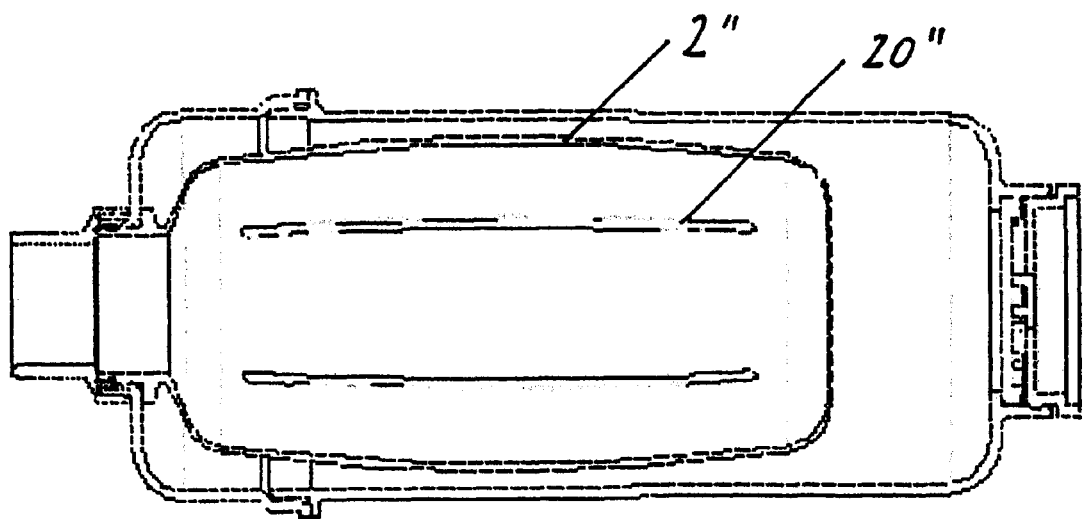

The term "suitable pharmaceuticals" as used herein, includes active ingredients, medicaments, compounds, compositions, or mixtures of substances bringing about a pharmacological, often advantageous, effect. It includes food, food supplements, nutrients, medicaments, vaccines, vitamins, and other useful active ingredients. Moreover, the terms, as used herein, include any physiologically or pharmacologically active substances, bringing about a topical or systemic effect in a patient. The active ingredient lending itself to administration in the form of an aerosol can be an antibody, antiviral active ingredient, anti-epileptic, analgesic, anti-inflammatory active ingredient, and bronchodilator or can be an organic or inorganic compound, which without any restrictions can also be a medicament having an effect on the peripheral nervous system, adrenergic receptors, cholinergic receptors, skeletal muscles, cardiovascular system, unstriated muscles, circulatory system, neuronal connections, endocrine and hormonic system, immune system, reproductive system, skeletal system, food supply system and excretory system, histamine cascade or central nervous system. Suitable active ingredients are for instance polysaccharides, steroids, hypnotics and sedatives, activators, tranquilizers, anticonvulsives (antispasmodics) and muscle-relaxants, anti-Parkinson-substances, analgesics, anti-inflammatory agents, antimicrobial active ingredients, antimalarial agents, hormones, including contraceptives, symphatocomimetics, polypeptides and proteins producing physiological effects, diuretics, substances regulating the lipometabolism, anti-androgenic active ingredients, antiparasitics, neoplastic and antineoplastic agents, antidiabetics, food and food supplements, growth-promoters, fats, stool-regulators, electrolytes, vaccines and diagnostics.

The invention is particularly suited for inhalation application of different active ingredients, such as the following ones (without being restricted thereto): Insulin, calcitonin, erythropoietin (EPO), factor VII, factor IX, cylcosporin, granulozyte colony stimulating factor (GCSF), alpha-1-proteinase inhibitor, elcatonin, granulocyte macrophage colony stimulating factor (GMCSF), growth hormones, human growth hormone (HGH), growth hormone releasing hormone (GHRH), heparin, low molecular weight heparin (LMWH), interferon alpha, interferon beta, interferon gamma, interleukin-2, luteinizing hormone releasing hormone (LHRH), somatostatin, somatostatin-analogs, including octreotides, vasopressin analogs, follicle stimulating hormone (FSH), insulin-like growth factor, insulintropin, interleukin-I receptor antagonist, interleukin-3, interleukin-4, interleukin-6, macrophage colony stimulating factor (M-CSF), nerve growth factor, parathryoid hormone (PTH), thymosin alpha 1, IIb/IIIa inhibitor, alpha-1 antitrypsin, antibodies against respiratorily syncytic virus, cystic fibrosis transmembrane regulator gene (CFTR), desoxyribonuclease (Dnase), bactericides, permeability increasing protein (BPI), anti-CMV antibodies, interleukin-1-receptor, retinol, retinyl-ester, tocopherols and their esters, tocotrienols and their esters, carotinoids, in particular beta carotin and other natural and synthetic antioxidants, retinol acids, pentamides, albuterolsulfate, metaproterenolsulfate, beclomethasonedipropionate, triamcinolonacetamide, budesonidacetonides, ipratropium bromide, flunisolides, fluticasones, cromolyn potassium, ergotamine tartrate and the analogs, agonists and antagonists of the above-mentioned substances. Moreover, active ingredients can be nucleic acids in the form of pure nucleic acid molecules, viral vectors, associated viral particles, nucleic acids associated with or contained in lipids or a lipid-containing material, plasmid DNA or plasmid RNA or other constructs from nucleic acids, which are suitable for cell transfection or cell transformation, in particular in the case of cells of the alveolar region of the lung. The active ingredient can be present in different forms, such as soluble or insoluble, charged or uncharged molecules, components of molecular complexes or pharmacologically acceptable inactive ingredients. The active ingredient can consist of naturally occurring molecules or their recombinant products, or the molecules can be analogs of the naturally occurring or recombinantly produced active ingredients to which or from which one or more amino acids have been added or deleted. Moreover, the active ingredient can contain attenuated live vaccines or killed viruses for vaccination purposes. If the active ingredient is insulin, it includes naturally extracted human insulin, recombinant human insulin, insulin extracted from cattle and/or swine, recombinant porcine or bovine insulin and mixtures of the above-mentioned insulins. The insulin can be present in a purified, that is a substantially purified form, but can also contain usual commercial extracts. The term "insulin" also includes analogs, to which or from which one or more amino acids of the naturally occurring or recombinant insulin have been added or deleted. The inhalation device according to the invention is particularly suited for the administration of vitamin A or vitamin A ester and retinoic acid or retinoic acid ester, also in combination with natural or synthetic antioxidants.

BRIEF DESCRIPTION OF THE DRAWINGS

The invention is hereinafter described in more detail with reference to the appended drawings:

FIG. 1 shows a longitudinal section of the inhalation device of the invention;

FIG. 2 shows a cross section of a first embodiment of the control means of the invention;

FIG. 3 shows a sketched perspective of the container of the inhalation device according to the invention;

FIG. 4 shows a longitudinal section of the second embodiment of the control means;

FIG. 5 shows a cross section of the control means according to FIG. 4;

FIG. 6 shows a longitudinal section of a third embodiment of the control means;

FIG. 7 shows a cross section of the control means according to FIG. 6;

FIG. 8 shows a plan view of a fourth embodiment of the control means;

FIG. 9 shows a cross section of the control means according to FIG. 8;

FIGS. 10*a* and 10*b* show sectional views of two alternative embodiments of the container;

FIG. 11 shows a modified version of the fourth embodiment;

FIG. 12 shows a further modified version of the fourth embodiment;

FIG. 13 shows an embodiment of the flexible mat; FIG. 14 shows an alternative embodiment of the flexible mat; and FIGS. 15*a* and 15*b* show a plan view and a sectional view of a disc with ribs, respectively.

DESCRIPTION OF PREFERRED EMBODIMENTS

The inhalation device 1 shown in FIG. 1 has a housing 12, the interior 13 of which comprises a container 2 (for instance a balloon or bag) for the aerosol volume. Starting from a mouthpiece 14, a channel 15 extends into the interior 13 of the housing 12. At this end, the channel 15 is shaped like a collar 19, onto which the container 2 can be pushed. The container 2 is preferably a one-way container. The container 2 is preferably at least in part made from a transparent material .

The channel 15 has a collar 16 which together with the nozzle 18 forms an arrangement 4 through which an aerosol (for instance vitamin A) can be dispensed from a cartridge 17 into the interior of the container. The nozzle 18 is preferably a nebulizer pointing into the interior of container 2. The container is self-expandable, with the result that a nebulization of the aerosol produces an expansion of the container. As shown in FIG. 10a, the container is preferably an expansion bellows 2'. FIG. 10b shows the embodiment with a bag 2" possessing reinforcing ribs 20" which ensure proper unfolding.

Figure 2:
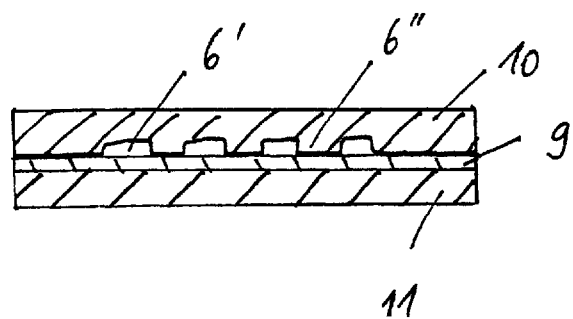

In the embodiment of the inhalation device of the invention shown in FIG. 1, a wall 10 of the housing 12 represents a wall which at the same time delimits a flow channel 6. This flow channel is further delimited by an oblong, flexible, large surface silicone wall (mat) 9 arranged in parallel to the wall 10. At the two ends of the flow channel are an inlet opening 7 and an outlet opening 8. As soon as a negative pressure is created in the interior of the housing by inhalation, air is sucked into the interior of the flow channel through the inlet opening 7 and flows through it as well as through the outlet opening 8 into the interior 13 of the housing 12. The negative pressure acting upon the silicone mat 9 has the result that the silicone mat bends or bulges towards the inside and reduces the cross section of the flow channel. The existing negative pressure decreases in the longitudinal direction of the flow channel from the outlet opening 8 towards the inlet opening 7. The silicone mat 9 is covered by a cover 11. The outlet opening 7 is provided in this cover. In a preferred embodiment, the flow channel 6 comprises several depressions 6' which are spaced apart from each other by corresponding longitudinal ribs 6". This is shown in FIG. 2.

Figure 3:
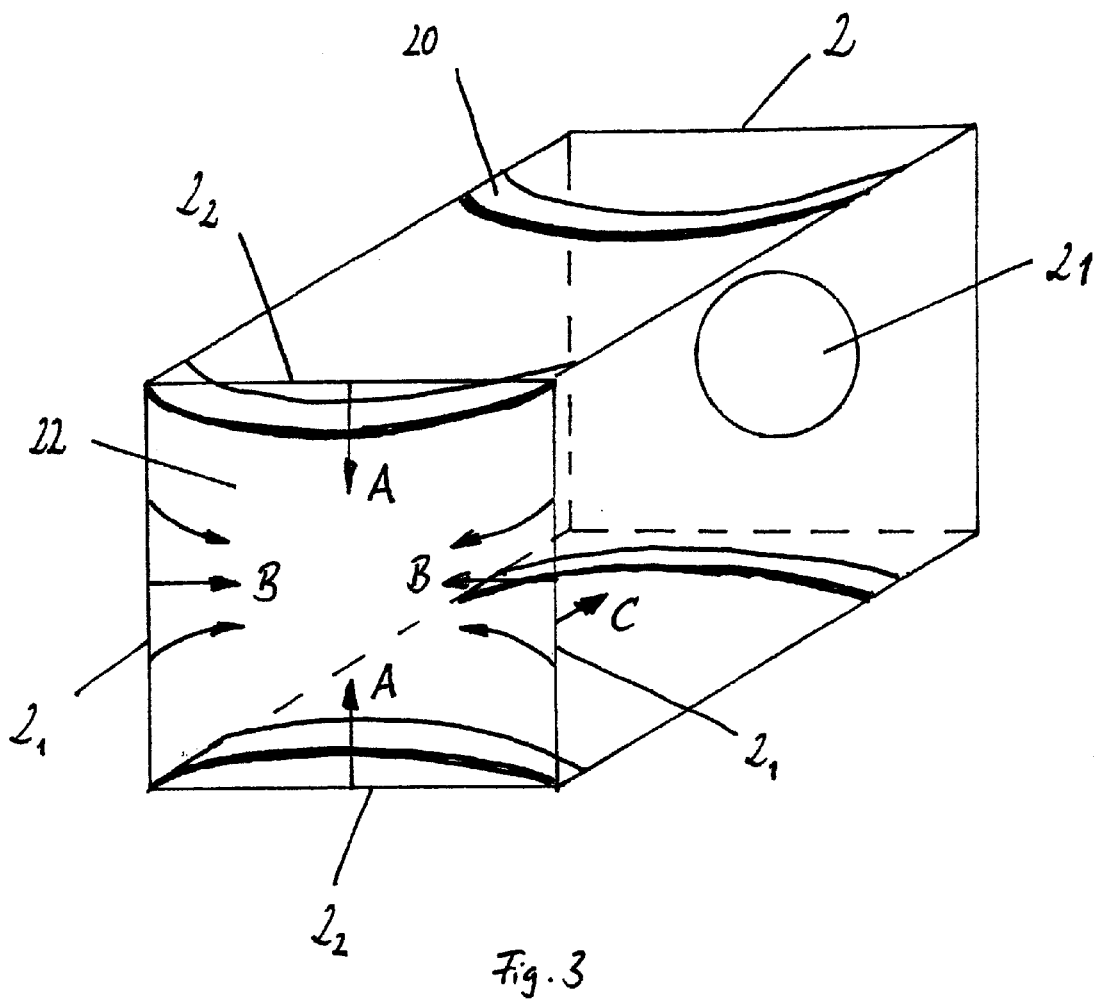

The container 2 preferably has at least one bracing 20. The embodiment of the container 2 shown in FIGS. 1 and 3 has four bracings 20. They are preferably arcuated and point into the interior of the container 2. The bracings 20, spaced apart from each other, are arranged at opposite walls of the container 2 in such a way that two bracings each are opposite to one another. The bracings 20 preferably run in a direction perpendicular to the channel 15. These bracings help the container 2 to fold up in a defined manner during inhalation. During inhalation, the horizontal walls 22 of the container 2 move towards each other in the direction of arrow A, while the vertical walls 21 fold towards the inside in the direction of arrow B. The wall 22 of the container 2 opposite the opening 21 moves in the direction of arrow C towards the opening 21. This defined folding of the container 2 permits an almost complete inhalation of the aerosol volume, as the container 2 contracts in a defined manner at the opening 21 and essentially no dead spaces are formed.

Figure 4:
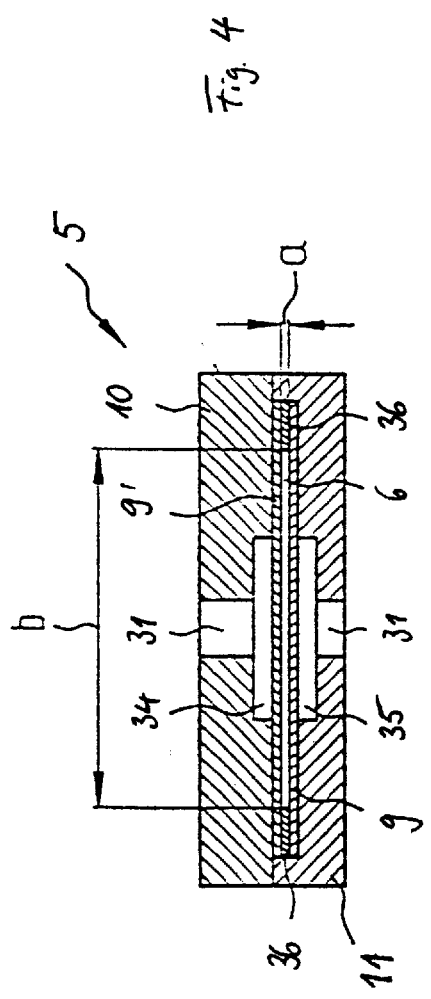
Figure 5:
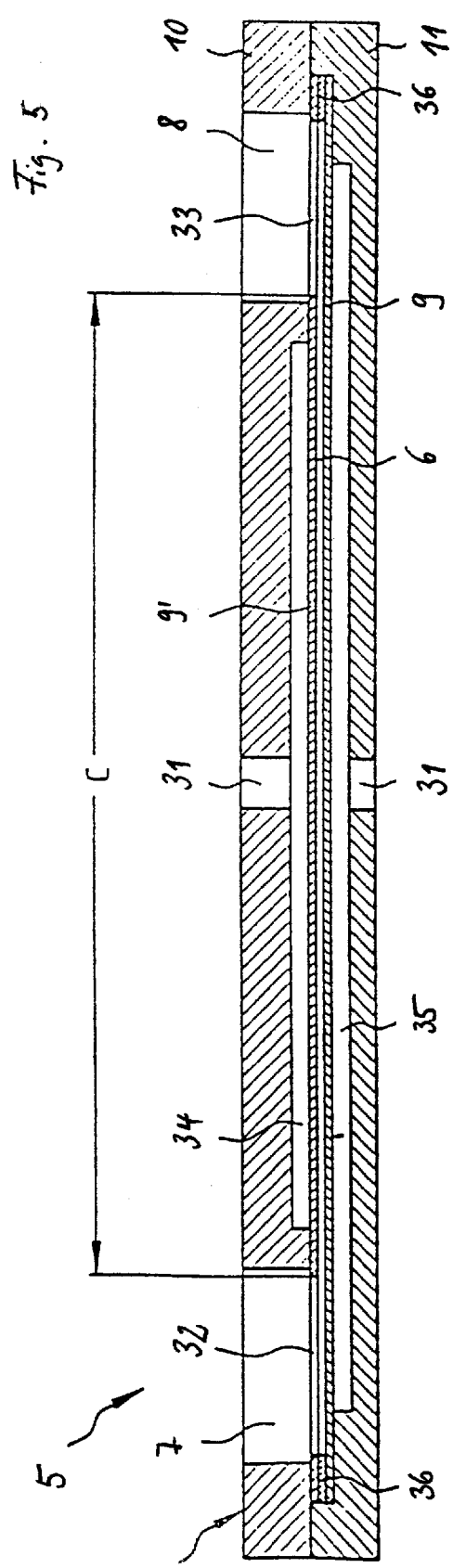

FIG. 4 shows a second embodiment of the control means. This control means consists of the first housing wall 10 and the cover 11. The wall 10 comprises an inlet opening 7 and an outlet opening 8. These openings communicate with each other via a flow channel 6 which is formed by two flexible mats 9, 9'. The mat 9' moreover comprises the openings 32, 33. Between the two flexible mats there is a spacer mat 36. This spacer mat 36 provides a flow channel 6 having a width b and a height a (see FIG. 4). The length of the flow channel 6 is indicated as c. The wall 10 and the cover 11 have compartment-like recesses 34, 36, which are open to the outside because of the aeration openings 31.

As soon as air is aspirated through the outlet opening 8, the flow channel 6 is imparted a negative pressure with the result that the two flexible mats 9, 9' bulge to the inside and thus reduce the cross section of the flow channel 6. In the course of this, the cross section of the flow channel 6 changes in dependency of the pressure difference between the outlet opening 8 and the inlet opening 7. As the flow volume in turn depends on the cross section of the flow channel 6, the flow volume is directly regulated by this change in the cross section. The flow volume is thus kept essentially constant.

Due to the digressive flexibility of the material of the flexible mats, the strength necessary for the bulging of the mats increases as the negative pressure in the flow channel 6 increases until the negative pressure reaches a limit value, which determines the desired minimum cross section of the flow channel for limiting the flow volume. Consequently, this embodiment also provides a control means which adjusts the flow volume to a constant value at pressures as low as 10 mbar, and preferably 5 to 10 mbar.

Figure 6:
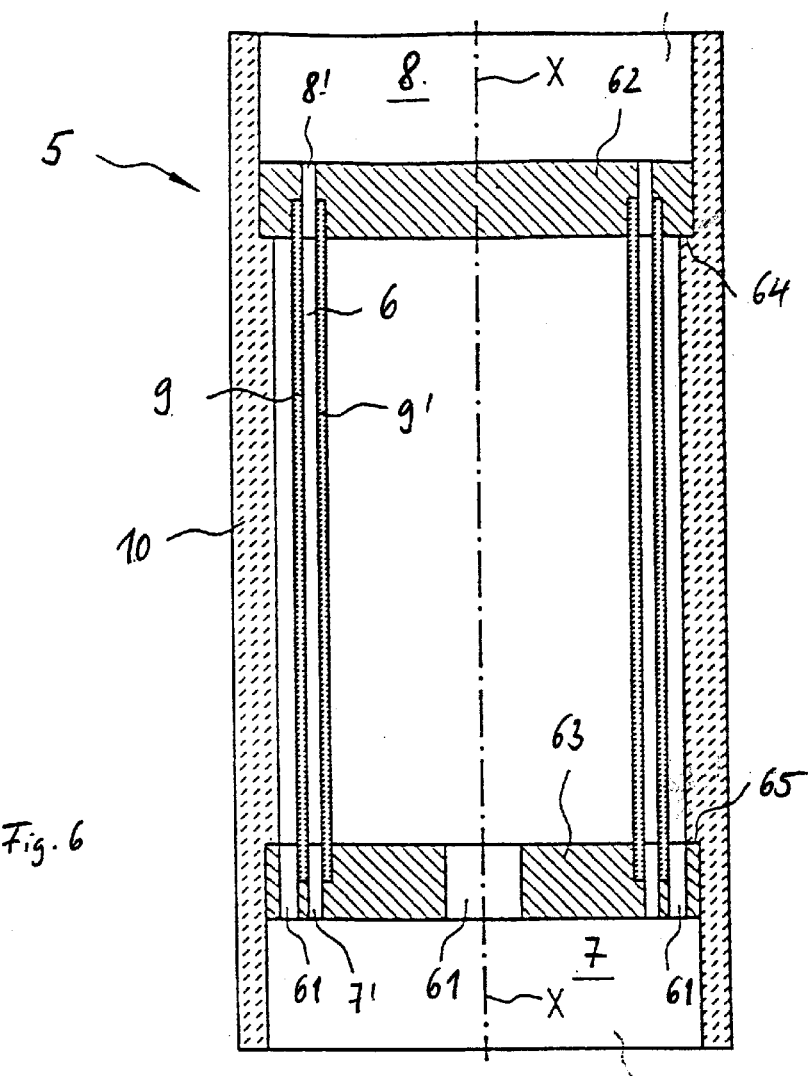
Figure 7:
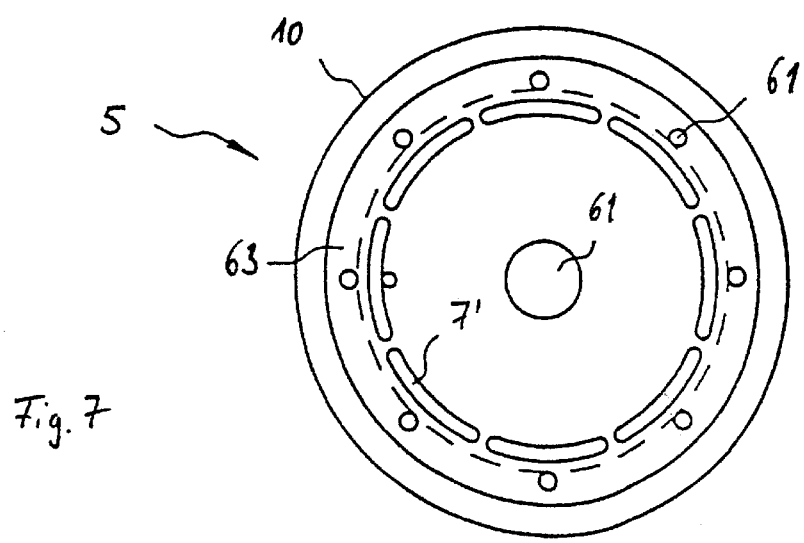

FIGS. 6 and 7 show a third embodiment. The cylindrical housing 10 has support discs 62, 63, which are spaced apart from each other and between which an annular flow channel 6 extends. This channel is formed by two flexible mats 9, 9'. The air supplied through the inlet opening 7 flows via the opening 7' in the support disc 63 through the flow channel 6 to the opening 8' in the support disc 62 to the outlet opening 8. This embodiment has pressure equalizer openings 61 in the support disc 63. The support discs 62 and 63 rest on the shoulders 64, 65 of the cylindrical housing 10.

Figure 8:
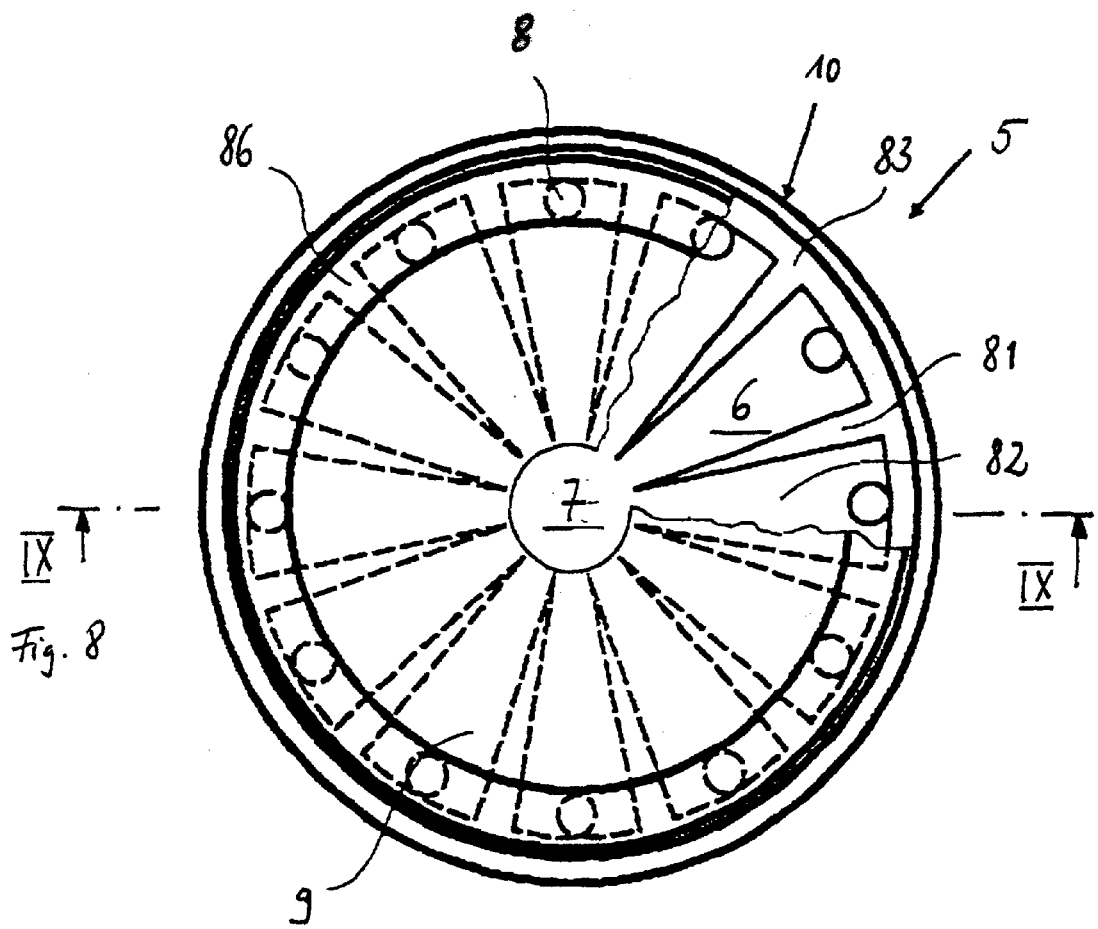
Figure 9:
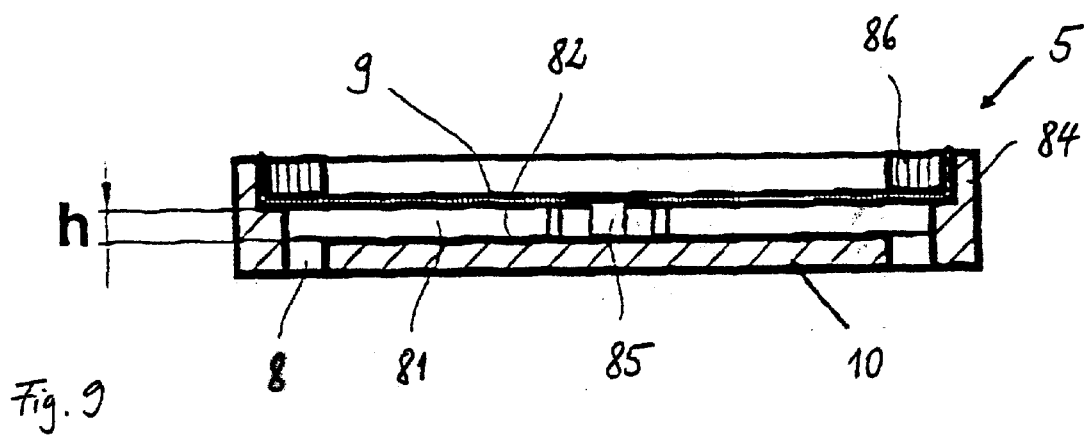

FIGS. 8 and 9 show a control means according to another embodiment. Here, the control means consists of a disc-shaped wall 10 comprising a disc-shaped recess 85. In the recess 85 are ribs 81 having the height h, which form flow channels 6. The flow channels 6 connect a central inlet opening 7 to the annularly arranged outlet openings 8. The recess of the disc-shaped wall 10 has a stepped area 84 in which a flexible mat 9 comes to lie. Mat 9 is clamped at the edge to the wall 10 by means of a ring fastener 86. The inlet opening 7 in the mat 9 is provided in the form of a central opening.

In the control means depicted in the Figures, air flows via the central inlet opening 7 through the flow channels 6, arranged in the form of a star, towards the outlet openings 8. The negative pressure thereby formed causes the flexible mat 9 to bulge into the flow channels in the same way as in the embodiment depicted in FIG. 2 and the mat thus reduces the cross section of the flow channel. Alternatively, the air can flow in the reverse direction.

Figure 11:
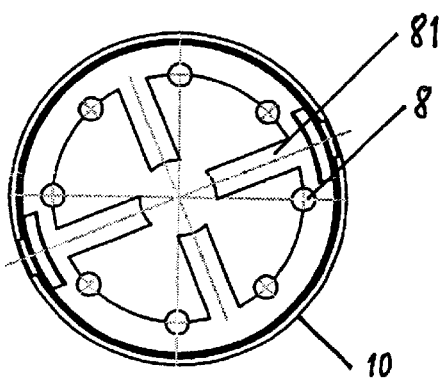
Figure 12:
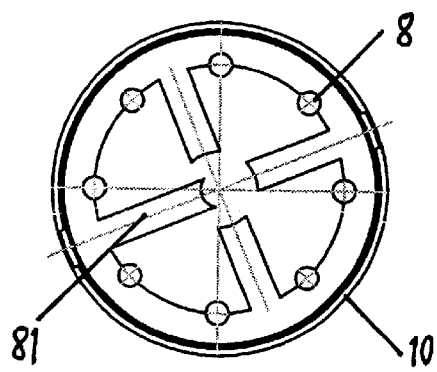
Figure 13:
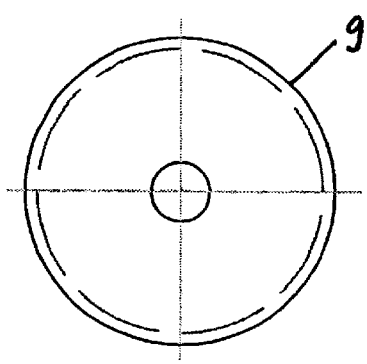
Figure 14:
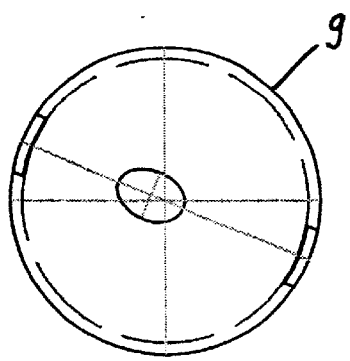

FIG. 11 shows an embodiment of the control means slightly modified compared to the embodiment of FIG. 8. This control means has four ribs 81, spaced approximately 90° apart, between each of which two outlet openings 8 are provided. The outlet openings are connected to the inlet opening 7 via flow channels formed between the ribs. The inlet opening in the mat 9 is either circular and arranged in the center (FIG. 13) or is oval and/or arranged eccentrically (FIG. 14). In a further modified embodiment (FIG. 12), one web is longer than the others (This is the web identified by numeral 81 in the drawing.). This modification prevents the mat 9 from closing the flow channel completely, as the mat cannot lie upon the disc-shaped wall 10 completely in the center. The oval opening in the mat 9 (see FIG. 14) also prevents the channel from closing completely.

Figure 15B:
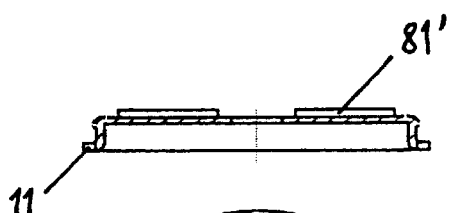
Figure 15A:
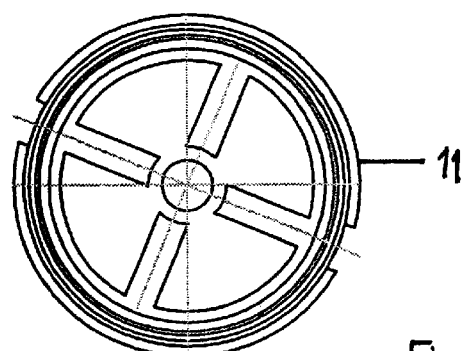

Moreover, it is preferred to provide the ribs not only in the disc-shaped wall 10, but also in a wall arranged on the other side of the mat 9 or in a circular disc 11 (see FIGS. 15a, 15b), by which the mat is supported on the other side. These are indicated by ribs 81' shown in the Figures. Due to the formation of ribs on both sides, the inhalation device can be used easily in any position (horizontal, vertical, at an angle), because the mat 9 is maintained in its position on both sides by the ribs. The central opening of the opposite disc 11 is at least as big as the opening in the mat.

FIG. 10*a* shows a cylindrical inhalation device which uses a gangway bellows 2' as the container. (In FIG. 10*b*, a bag 2" with reinforcing ribs 20" is shown.) On one end, as shown on the left-hand side in the drawing, there is the opening through which aerosol is supplied from the container to the patient. On the other end, as shown on the right-hand side in the drawing, there is a control means according to FIGS. 11 and 12, respectively.

Apart from the self-expandable container 2 for a predetermined aerosol volume and the apparatus 4 for introducing aerosol (for instance retinol, retinyl ester, retinoic acid or retinoic acid ester) from an aerosol dispenser 17 into the container 2, the inhalation device according to the invention preferably comprises one of the controllers depicted in FIGS. 2 and 4 to 9, for controlling the inhalation flow.

We claim:

1. An inhalation device comprising:

a self-expandable container for a predetermined aerosol volume;

a means for introducing aerosol from an aerosol dispenser into the container; and a control means for controlling the inhalation flow, wherein the control means keeps the inhalation flow essentially constant during the entire inhalation period.

2. The inhalation device according to claim 1, wherein the control means has an oblong flow channel comprising an inlet opening and an outlet opening, and wherein the flow channel has an essentially flat cross section, and wherein the flow channel is delimited by at least one flexible large surface wall extending along the flow channel.

3. The inhalation device according to claim 2, wherein the at least one flexible wall reduces the cross section of the flow channel via the negative pressure produced by an inhalation of the aerosol.

4. The inhalation device according to claim 2, wherein the flow channel is additionally delimited by a first essentially stiff wall.

5. The inhalation device according to claim 4, wherein the first, essentially stiff wall has one or more depressions which extend in the direction of the channel and are separated from each other by ribs.

6. The inhalation device according to claim 2, wherein the at least one flexible wall is arranged between the at least one stiff wall and a cover.

7. The inhalation device according to claim 4, wherein the outlet opening is arranged in the at least one stiff wall.

8. The inhalation device according to claim 6, wherein the inlet opening is arranged in the cover.

9. The inhalation device according to claim 2 further comprising a second flexible wall which is arranged in parallel to the first flexible wall and forms the flow channel together with said first flexible wall.

10. The inhalation device according to claim 2, wherein the inlet opening and the outlet opening are arranged perpendicularly to the flow channel.

11. The inhalation device according to claim 2, wherein the at least one flexible wall is made of a bio-compatible material.

12. The inhalation device according to claim 1 further comprising a housing for the container.

13. The inhalation device according to claim 12, wherein the first essentially stiff wall is integrally formed with the housing.

14. The inhalation device according to claim 13, wherein the outlet opening connects the flow channel to the interior of the housing.

15. The inhalation device according to claim 1, wherein the control means comprises an oblong flow channel which has an inlet opening and an outlet opening and has an essentially annular cross section.

16. The inhalation device according to claim 15, wherein the flow channel is formed by two flexible walls spaced apart from each other.

17. The inhalation device according to claim 1, wherein the control means comprises at least one flow channel radially extending between a central inlet opening and at least one outlet opening radially spaced apart from the inlet opening.

18. The inhalation device according to claim 17, wherein the at least one radially extending flow channel is formed by ribs which form a star and extend from an essentially stiff wall to an essentially flexible wall.

19. The inhalation device according to claim 18, wherein the ribs are of equal length or at least one web is longer than the others.

20. The inhalation device according to claim 1 wherein a channel connects a mouthpiece to the interior of the housing and extends into the interior of the housing and has a collar at its end there.

21. The inhalation device according to claim 20, wherein the container can be attached to the collar.

22. The inhalation device according to claim 20, wherein the means for introducing aerosol from an aerosol dispenser is arranged at the channel.

23. The inhalation device according to claim 1, wherein the introduction means has a holder for a cartridge.

24. The inhalation device according to claim 1, wherein the introduction means has a holder for a cartridge comprising a nozzle, wherein the nozzle is a nebulizer.

25. The inhalation device according to claim 1, wherein the container is a bag, a balloon, or an expansion bellows.

26. The inhalation device according to claim 1, wherein the aerosol contains vitamin A.

27. The inhalation device according to claim 1, wherein the container is a bag, a balloon, or an expansion bellows, each consisting of a bio-compatible material.

* * * * *